United States Patent
Hogan et al.

(10) Patent No.: US 12,270,076 B2
(45) Date of Patent: Apr. 8, 2025

(54) METHOD FOR IDENTIFYING MASTITIS-CAUSING MICROBES

(71) Applicants: Michael E. Hogan, Stony Brook, NY (US); Frederick H. Eggers, Sahuarita, AZ (US); Melissa R. May, Tucson, AZ (US)

(72) Inventors: Michael E. Hogan, Stony Brook, NY (US); Frederick H. Eggers, Sahuarita, AZ (US); Melissa R. May, Tucson, AZ (US)

( * ) Notice: Subject to any disclaimer, the term of this patent is extended or adjusted under 35 U.S.C. 154(b) by 716 days.

(21) Appl. No.: 17/087,099

(22) Filed: Nov. 2, 2020

(65) Prior Publication Data

US 2021/0130898 A1    May 6, 2021

Related U.S. Application Data

(60) Provisional application No. 62/928,899, filed on Oct. 31, 2019.

(51) Int. Cl.
| | | |
|---|---|---|
| *C12Q 1/68* | (2018.01) | |
| *C12N 1/14* | (2006.01) | |
| *C12N 1/20* | (2006.01) | |
| *C12Q 1/6832* | (2018.01) | |
| *C12Q 1/6834* | (2018.01) | |
| *C12Q 1/6874* | (2018.01) | |
| *C12Q 1/6888* | (2018.01) | |
| *C12N 1/12* | (2006.01) | |

(52) U.S. Cl.
CPC ............ *C12Q 1/6874* (2013.01); *C12N 1/14* (2013.01); *C12N 1/20* (2013.01); *C12Q 1/6832* (2013.01); *C12Q 1/6834* (2013.01); *C12Q 1/6888* (2013.01); *C12N 1/12* (2013.01); *C12Q 2600/124* (2013.01)

(58) Field of Classification Search
CPC .. C12Q 1/6874; C12Q 1/6832; C12Q 1/6834; C12Q 1/6888; C12Q 2600/124; C12N 1/12
See application file for complete search history.

(56) References Cited

U.S. PATENT DOCUMENTS

2022/0288135 A1* 9/2022 Starzl .................... A61P 31/04

OTHER PUBLICATIONS

Giannino et al. (J of Microbiol Methods, 78, 2009, 181-188) (Year: 2009).*

* cited by examiner

*Primary Examiner* — Stephanie K Mummert
(74) *Attorney, Agent, or Firm* — Benjamin Aaron Adler

(57) ABSTRACT

Provided herein is a method for identifying a mastitis-causing microbe in a subject. A milk sample is centrifuged to form a microbial pellet, total nucleic acids are extracted from the pellet and a microarray analysis of extracted DNA from which the mastitis-causing microbe is identified from DNA hybridization to mastitis-causing microbe species-specific gene probes. Also provided is a method for diagnosing a bovine mastitis infection in a dairy cow after identifying the bovine mastitis-causing microbe in a raw milk sample from the dairy cow.

8 Claims, 8 Drawing Sheets
Specification includes a Sequence Listing.

Milk Sample F

Milk Sample G

SAMPLE F1: 4°C x 15 minutes

SAMPLE F2: 25°C x 15 minutes

SAMPLE F3: 37°C x 15 minutes

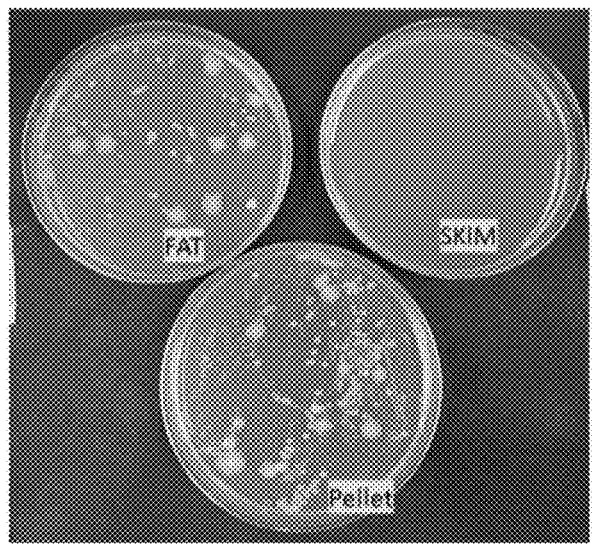
FIG. 8A
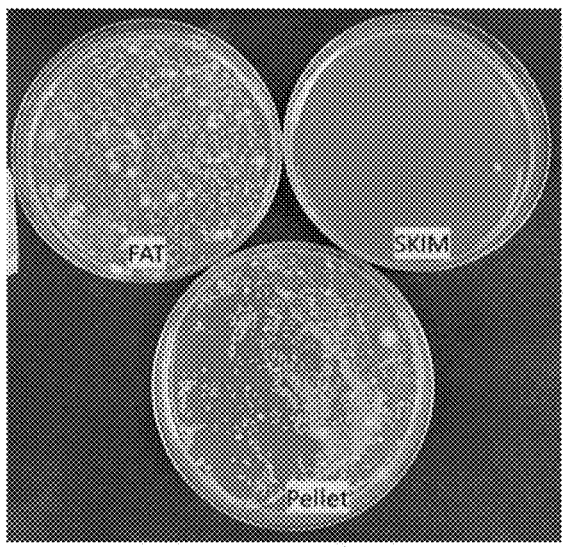
FIG. 8B
FIG. 8C
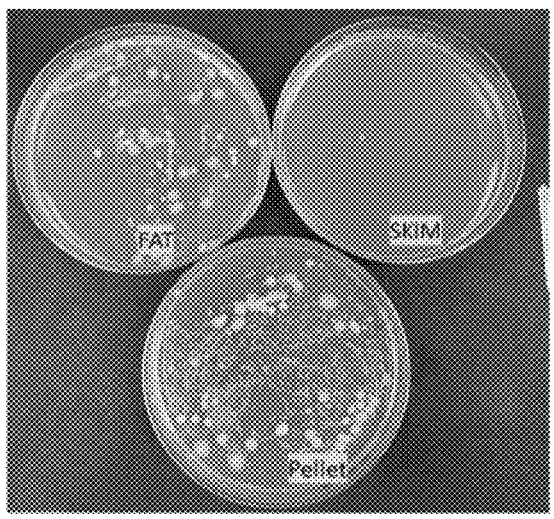

SEQUENCE LISTING

```
<160> NUMBER OF SEQ ID NOS: 61

<210> SEQ ID NO 1
<211> LENGTH: 23
<212> TYPE: DNA
<213> ORGANISM: Artificial Sequence
<220> FEATURE:
<223> OTHER INFORMATION: Forward primer for amplification of the 16S
      rDNA HV3 locus in all bacteria

<400> SEQUENCE: 1
tttcacaytg gractgagac acg                                              23

<210> SEQ ID NO 2
<211> LENGTH: 27
<212> TYPE: DNA
<213> ORGANISM: Artificial Sequence
<220> FEATURE:
<223> OTHER INFORMATION: Reverse primer for amplification of the 16S
      rDNA HV3 locus in all bacteria

<400> SEQUENCE: 2
tttgactacc agggtatcta atcctgt                                          27

<210> SEQ ID NO 3
<211> LENGTH: 28
<212> TYPE: DNA
<213> ORGANISM: Artificial Sequence
<220> FEATURE:
<223> OTHER INFORMATION: Forward primer for amplification of the Stx1
      locus in pathogenic Escherichia coli

<400> SEQUENCE: 3
tttataatct acggcttatt gttgaacg                                         28

<210> SEQ ID NO 4
<211> LENGTH: 29
<212> TYPE: DNA
<213> ORGANISM: Artificial Sequence
<220> FEATURE:
<223> OTHER INFORMATION: Reverse primer for amplification of the Stx1
      locus in pathogenic Escherichia coli

<400> SEQUENCE: 4
tttggtatag ctactgtcac cagacaatg                                        29

<210> SEQ ID NO 5
<211> LENGTH: 26
<212> TYPE: DNA
<213> ORGANISM: Artificial Sequence
<220> FEATURE:
<223> OTHER INFORMATION: Forward primer for amplification of the Stx2
      locus in pathogenic Escherichia coli

<400> SEQUENCE: 5
```
tttgatgcat ccagagcagt tctgcg                                          26

<210> SEQ ID NO 6
<211> LENGTH: 27
<212> TYPE: DNA
<213> ORGANISM: Artificial Sequence
<220> FEATURE:
<223> OTHER INFORMATION: Reverse primer for amplification of the Stx2
      locus in pathogenic Escherichia coli

<400> SEQUENCE: 6
tttgtgaggt ccacgtctcc cggcgtc                                         27

<210> SEQ ID NO 7
<211> LENGTH: 26
<212> TYPE: DNA
<213> ORGANISM: Artificial Sequence
<220> FEATURE:
<223> OTHER INFORMATION: Forward primer for amplification of the tuf
      locus in all Escherichia coli

<400> SEQUENCE: 7
tttcagagtg ggaagcgaaa atcctg                                          26

<210> SEQ ID NO 8
<211> LENGTH: 26
<212> TYPE: DNA
<213> ORGANISM: Artificial Sequence
<220> FEATURE:
<223> OTHER INFORMATION: Reverse primer for amplification of the tuf
      locus in all Escherichia coli

<400> SEQUENCE: 8
tttacgccag tacaggtaga cttctg                                          26

<210> SEQ ID NO 9
<211> LENGTH: 30
<212> TYPE: DNA
<213> ORGANISM: Artificial Sequence
<220> FEATURE:
<223> OTHER INFORMATION: Forward primer for amplification of the 16S
      rDNA HV3 locus in Enterobacteriaceae

<400> SEQUENCE: 9
ttaccttcgg gcctcttgcc atcrgatgtg                                      30

<210> SEQ ID NO 10
<211> LENGTH: 33
<212> TYPE: DNA
<213> ORGANISM: Artificial Sequence
<220> FEATURE:
<223> OTHER INFORMATION: Reverse primer for amplification of the 16S
      rDNA HV3 locus in Enterobacteriaceae

<400> SEQUENCE: 10
ttggaattct acccccctct acragactca agc                                  33

<210> SEQ ID NO 11
<211> LENGTH: 26
<212> TYPE: DNA
<213> ORGANISM: Artificial Sequence
<220> FEATURE:
<223> OTHER INFORMATION: Forward primer for amplification of the ITS2
      locus in all yeast and mold/fungi

<400> SEQUENCE: 11
tttactttya acaayggatc tcttgg                                          26

<210> SEQ ID NO 12
<211> LENGTH: 26
<212> TYPE: DNA
<213> ORGANISM: Artificial Sequence
<220> FEATURE:
<223> OTHER INFORMATION: Reverse primer for amplification of the ITS2
      locus in all yeast and mold/fungi

<400> SEQUENCE: 12
tttcttttcc tccgcttatt gatatg                                      26

<210> SEQ ID NO 13
<211> LENGTH: 28
<212> TYPE: DNA
<213> ORGANISM: Artificial Sequence
<220> FEATURE:
<223> OTHER INFORMATION: Forward primer for amplification of the ITS2
      locus in Aspergillus spp

<400> SEQUENCE: 13
tttaaaggca gcggcggcac cgcgtccg                                    28

<210> SEQ ID NO 14
<211> LENGTH: 27
<212> TYPE: DNA
<213> ORGANISM: Artificial Sequence
<220> FEATURE:
<223> OTHER INFORMATION: Reverse primer for amplification of the ITS2
      locus in Aspergillus spp

<400> SEQUENCE: 14
ttttcttttc ctccgcttat tgatatg                                     27

<210> SEQ ID NO 15
<211> LENGTH: 24
<212> TYPE: DNA
<213> ORGANISM: Artificial Sequence
<220> FEATURE:
<223> OTHER INFORMATION: Forward primer for amplification of the 16S
      rDNA HV3 locus in all bacteria

<400> SEQUENCE: 15
tttactgaga cacggyccar actc                                        24

<210> SEQ ID NO 16
<211> LENGTH: 24
<212> TYPE: DNA
<213> ORGANISM: Artificial Sequence
<220> FEATURE:
<223> OTHER INFORMATION: Reverse primer for amplification of the 16S
      rDNA HV3 Locus in all bacteria

<400> SEQUENCE: 16
tttgtattac cgcggctgct ggca                                        24

<210> SEQ ID NO 17
<211> LENGTH: 28
<212> TYPE: DNA
<213> ORGANISM: Artificial Sequence
<220> FEATURE:
<223> OTHER INFORMATION: Forward primer for amplification of the Stx1
      locus in pathogenic Escherichia coli

<400> SEQUENCE: 17
tttatgtgac aggatttgtt aacaggac                                    28

<210> SEQ ID NO 18
<211> LENGTH: 28
<212> TYPE: DNA
<213> ORGANISM: Artificial Sequence
<220> FEATURE:
<223> OTHER INFORMATION: Reverse primer for amplification of the Stx1
      locus in pathogenic Escherichia coli

<400> SEQUENCE: 18
tttctgtcac cagacaatgt aaccgctg                                    28

<210> SEQ ID NO 19
<211> LENGTH: 24
<212> TYPE: DNA
<213> ORGANISM: Artificial Sequence
<220> FEATURE:
<223> OTHER INFORMATION: Forward primer for amplification of the Stx2
      locus in pathogenic Escherichia coli

<400> SEQUENCE: 19 tttttgtcact gtcacagcag aag    24

<210> SEQ ID NO 20
<211> LENGTH: 25
<212> TYPE: DNA
<213> ORGANISM: Artificial Sequence
<220> FEATURE:
<223> OTHER INFORMATION: Reverse primer for amplification of the Stx2
      locus in pathogenic Escherichia coli

<400> SEQUENCE: 20
tttgcgtcat cgtatacaca ggagc                                       25

<210> SEQ ID NO 21
<211> LENGTH: 25
<212> TYPE: DNA
<213> ORGANISM: Artificial Sequence
<220> FEATURE:
<223> OTHER INFORMATION: Forward primer for amplification of the tuf
      locus in all Escherichia coli

<400> SEQUENCE: 21
tttgttgtta ccggtcgtgt agaac                                       25

<210> SEQ ID NO 22
<211> LENGTH: 28
<212> TYPE: DNA
<213> ORGANISM: Artificial Sequence
<220> FEATURE:
<223> OTHER INFORMATION: Reverse primer for amplification of the tuf
      locus in all Escherichia coli

<400> SEQUENCE: 22
tttcttctga gtctctttga taccaacg                                    28

<210> SEQ ID NO 23
<211> LENGTH: 30
<212> TYPE: DNA
<213> ORGANISM: Artificial Sequence
<220> FEATURE:
<223> OTHER INFORMATION: Forward primer for amplification of the 16S
      rDNA HV3 locus in Enterobacteriaceae

<400> SEQUENCE: 23
ttatattgca caatgggcgc aagcctgatg                                  30

<210> SEQ ID NO 24

```
<211> LENGTH: 25
<212> TYPE: DNA
<213> ORGANISM: Artificial Sequence
<220> FEATURE:
<223> OTHER INFORMATION: Reverse primer for amplification of the 16S
      rDNA HV3 locus in Enterobacteriaceae

<400> SEQUENCE: 24
ttttgtatta ccgcggctgc tggca                                         25

<210> SEQ ID NO 25
<211> LENGTH: 23
<212> TYPE: DNA
<213> ORGANISM: Artificial Sequence
<220> FEATURE:
<223> OTHER INFORMATION: Forward primer for amplification of the ITS2
      locus in all yeast and mold/fungi

<400> SEQUENCE: 25
tttgcatcga tgaagarcgy agc                                           23

<210> SEQ ID NO 26
<211> LENGTH: 22
<212> TYPE: DNA
<213> ORGANISM: Artificial Sequence
<220> FEATURE:
<223> OTHER INFORMATION: Reverse primer for amplification of the ITS2
      locus in all yeast and mold/fungi

<400> SEQUENCE: 26
tttcctccgc ttattgatat gc                                            22

<210> SEQ ID NO 27
<211> LENGTH: 26
<212> TYPE: DNA
<213> ORGANISM: Artificial Sequence
<220> FEATURE:
<223> OTHER INFORMATION: Forward primer for amplification of the ITS2
      locus in Aspergillus spp

<400> SEQUENCE: 27
tttcctcgag cgtatggggc tttgtc                                        26

<210> SEQ ID NO 28
<211> LENGTH: 24
<212> TYPE: DNA
<213> ORGANISM: Artificial Sequence
<220> FEATURE:
<223> OTHER INFORMATION: Reverse primer for amplification of the ITS2
      locus in Aspergillus spp

<400> SEQUENCE: 28
tttttcctcc gcttattgat atgc                                          24

<210> SEQ ID NO 29
<211> LENGTH: 26
<212> TYPE: DNA
<213> ORGANISM: Artificial Sequence
<220> FEATURE:
<223> OTHER INFORMATION: Forward RSG Primer for amplification all fungus

<400> SEQUENCE: 29
tttactttca acaayggatc tcttgg                                        26

<210> SEQ ID NO 30
<211> LENGTH: 23
<212> TYPE: DNA
```

-continued

<213> ORGANISM: Artificial Sequence
<220> FEATURE:
<223> OTHER INFORMATION: Reverse RSG Primer for amplification of all
      fungus

<400> SEQUENCE: 30
cttttcctcc gcttattgat atg                                      23

<210> SEQ ID NO 31
<211> LENGTH: 23
<212> TYPE: DNA
<213> ORGANISM: Artificial Sequence
<220> FEATURE:
<223> OTHER INFORMATION: Forward RSG Primer for amplification of all
      bacteria

<400> SEQUENCE: 31
tttcacactg gractgagac acg                                      23

<210> SEQ ID NO 32
<211> LENGTH: 24
<212> TYPE: DNA
<213> ORGANISM: Artificial Sequence
<220> FEATURE:
<223> OTHER INFORMATION: Reverse RSG Primer for amplification of all
      bacteria

<400> SEQUENCE: 32
ttttgtatta ccgcggctgc tggc                                     24

<210> SEQ ID NO 33
<211> LENGTH: 23
<212> TYPE: DNA
<213> ORGANISM: Artificial Sequence
<220> FEATURE:
<223> OTHER INFORMATION: Forward rimer for amplification of all fungus

<400> SEQUENCE: 33
tttgcatcga tgaagaacgc agc                                      23

<210> SEQ ID NO 34
<211> LENGTH: 23
<212> TYPE: DNA
<213> ORGANISM: Artificial Sequence
<220> FEATURE:
<223> OTHER INFORMATION: Reverse Primer for amplification of all fungus

<400> SEQUENCE: 34
ttttcctccg cttattgata tgc                                      23

<210> SEQ ID NO 35
<211> LENGTH: 24
<212> TYPE: DNA
<213> ORGANISM: Artificial Sequence
<220> FEATURE:
<223> OTHER INFORMATION: Forward Primer for amplification of all
      bacteria

<400> SEQUENCE: 35
tttcacactg gractgagac acgg                                     24

<210> SEQ ID NO 36
<211> LENGTH: 30
<212> TYPE: DNA
<213> ORGANISM: Artificial Sequence
<220> FEATURE:
<223> OTHER INFORMATION: Probe sequence for the 16S locus for total aerobic bacteria with high sensitivity

<400> SEQUENCE: 36
tttttttttc ctacgggagg cagttttttt                    30

<210> SEQ ID NO 37
<211> LENGTH: 30
<212> TYPE: DNA
<213> ORGANISM: Artificial Sequence
<220> FEATURE:
<223> OTHER INFORMATION: Probe sequence for the 16S locus for total
      aerobic bacteria with medium sensitivity

<400> SEQUENCE: 37
ttttttttcc ctacgggagg cattttttt                     30

<210> SEQ ID NO 38
<211> LENGTH: 30
<212> TYPE: DNA
<213> ORGANISM: Artificial Sequence
<220> FEATURE:
<223> OTHER INFORMATION: Probe sequence for the 16S locus for total
      aerobic bacteria with low sensitivity

<400> SEQUENCE: 38
tttattttcc ctacgggagg cttttatttt                    30

<210> SEQ ID NO 39
<211> LENGTH: 30
<212> TYPE: DNA
<213> ORGANISM: Artificial Sequence
<220> FEATURE:
<223> OTHER INFORMATION: Probe sequence for the 16S locus in
      Enterobacteriaceae with low sensitivity

<400> SEQUENCE: 39
tttattctat tgacgttacc catttatttt                    30

<210> SEQ ID NO 40
<211> LENGTH: 30
<212> TYPE: DNA
<213> ORGANISM: Artificial Sequence
<220> FEATURE:
<223> OTHER INFORMATION: Probe sequence for the 16S locus in
      Enterobacteriaceae with medium sensitivity

<400> SEQUENCE: 40 tttttctat tgacgttacc cgttttttt                      30

<210> SEQ ID NO 41
<211> LENGTH: 30
<212> TYPE: DNA
<213> ORGANISM: Artificial Sequence
<220> FEATURE:
<223> OTHER INFORMATION: Probe sequence for the 16S locus in Escherichia
      coli and Shigella

<400> SEQUENCE: 41
ttttctaata cctttgctca ttgactcttt                    30

<210> SEQ ID NO 42
<211> LENGTH: 30
<212> TYPE: DNA
<213> ORGANISM: Artificial Sequence
<220> FEATURE:
<223> OTHER INFORMATION: Probe sequence for the 16S locus in Escherichia
      coli and Shigella

```
<400> SEQUENCE: 42 tttttaagg gagtaaagtt aatatttttt                                    30

<210> SEQ ID NO 43
<211> LENGTH: 30
<212> TYPE: DNA
<213> ORGANISM: Artificial Sequence
<220> FEATURE:
<223> OTHER INFORMATION: Probe sequence for the 16S locus in Escherichia
      coli and Shigella

<400> SEQUENCE: 43
ttttctcctt tgctcattga cgttattttt                                   30

<210> SEQ ID NO 44
<211> LENGTH: 36
<212> TYPE: DNA
<213> ORGANISM: Artificial Sequence
<220> FEATURE:
<223> OTHER INFORMATION: Probe sequence for the 16S locus in
      bile-tolerant gram negative bacteria with high sensitivity

<400> SEQUENCE: 44
tttttctatg cagtcatgct gtgtgtrtgt ctttttt                           36

<210> SEQ ID NO 45
<211> LENGTH: 34
<212> TYPE: DNA
<213> ORGANISM: Artificial Sequence
<220> FEATURE:
<223> OTHER INFORMATION: Probe sequence for the 16S locus in
      bile-tolerant gram negative bacteria with medium sensitivity

<400> SEQUENCE: 45
tttttctatg cagccatgct gtgtgtrttt tttt                              34

<210> SEQ ID NO 46
<211> LENGTH: 34
<212> TYPE: DNA
<213> ORGANISM: Artificial Sequence
<220> FEATURE:
<223> OTHER INFORMATION: Probe sequence for the 16S locus in
      bile-tolerant gram negative bacteria with low sensitivity

<400> SEQUENCE: 46
tttttctatg cagtcatgct gcgtgtrttt tttt                              34

<210> SEQ ID NO 47
<211> LENGTH: 30
<212> TYPE: DNA
<213> ORGANISM: Artificial Sequence
<220> FEATURE:
<223> OTHER INFORMATION: Probe sequence for the 16S locus in Coliform
      and Enterobacteriaceae

<400> SEQUENCE: 47 tttttttctat tgacgttacc cgctttttt                                   30

<210> SEQ ID NO 48
<211> LENGTH: 34
<212> TYPE: DNA
<213> ORGANISM: Artificial Sequence
<220> FEATURE:
<223> OTHER INFORMATION: Probe sequence for bacterial etuf gene

<400> SEQUENCE: 48
``` tttttttccat caaagttggt gaagaatctt tttt              34

<210> SEQ ID NO 49
<211> LENGTH: 30
<212> TYPE: DNA
<213> ORGANISM: Artificial Sequence
<220> FEATURE:
<223> OTHER INFORMATION: Probe sequence for the 16S locus in Klebsiella
      oxytoca

<400> SEQUENCE: 49 tttttttctaa ccttattcat tgatctttt              30

<210> SEQ ID NO 50
<211> LENGTH: 30
<212> TYPE: DNA
<213> ORGANISM: Artificial Sequence
<220> FEATURE:
<223> OTHER INFORMATION: Probe sequence for the 16S locus in Klebsiella
      pneumoniae

<400> SEQUENCE: 50 tttttttctaa ccttggcgat tgatctttt              30

<210> SEQ ID NO 51
<211> LENGTH: 34
<212> TYPE: DNA
<213> ORGANISM: Artificial Sequence
<220> FEATURE:
<223> OTHER INFORMATION: Probe sequence for the 16S locus in Serratia
      spp.

<400> SEQUENCE: 51
tttattctgt gaacttaata cgttcattt tatt              34

<210> SEQ ID NO 52
<211> LENGTH: 34
<212> TYPE: DNA
<213> ORGANISM: Artificial Sequence
<220> FEATURE:
<223> OTHER INFORMATION: Probe sequence for the 16S locus in
      Staphylococcus aureus

<400> SEQUENCE: 52 tttatttca tatgtgtaag taactgtttt attt              34

<210> SEQ ID NO 53
<211> LENGTH: 30
<212> TYPE: DNA
<213> ORGANISM: Artificial Sequence
<220> FEATURE:
<223> OTHER INFORMATION: Probe sequence for the 16S locus in
      Staphylococcus aureus

<400> SEQUENCE: 53 tttttttcata tgtgtaagta actgttttt              30

<210> SEQ ID NO 54
<211> LENGTH: 38
<212> TYPE: DNA
<213> ORGANISM: Artificial Sequence
<220> FEATURE:
<223> OTHER INFORMATION: Probe sequence for the ITS2 locus in total
      yeast and mold with high sensitivity

<400> SEQUENCE: 54

```
tttttttttga atcatcgart ctttgaacgc attttttt          38
```

<210> SEQ ID NO 55
<211> LENGTH: 31
<212> TYPE: DNA
<213> ORGANISM: Artificial Sequence
<220> FEATURE:
<223> OTHER INFORMATION: Probe sequence for the ITS2 locus in total
      yeast and mold with low sensitivity

<400> SEQUENCE: 55

```
tttttttga atcatcgart ctcctttttt t                   31
```

<210> SEQ ID NO 56
<211> LENGTH: 36
<212> TYPE: DNA
<213> ORGANISM: Artificial Sequence
<220> FEATURE:
<223> OTHER INFORMATION: Probe sequence for the ITS2 locus in total
      yeast and mold with medium sensitivity

<400> SEQUENCE: 56

```
tttttttga atcatcgart ctttgaacgt tttttt              36
```

<210> SEQ ID NO 57
<211> LENGTH: 34
<212> TYPE: DNA
<213> ORGANISM: Artificial Sequence
<220> FEATURE:
<223> OTHER INFORMATION: Probe sequence for the ITS2 locus in
      Aspergillus fumigatus

<400> SEQUENCE: 57

```
tttcttttcg acacccaact ttatttcctt attt               34
```

<210> SEQ ID NO 58
<211> LENGTH: 30
<212> TYPE: DNA
<213> ORGANISM: Artificial Sequence
<220> FEATURE:
<223> OTHER INFORMATION: Probe sequence for the ITS2 locus in
      Aspergillus fumigatus

<400> SEQUENCE: 58

```
ttttttgcc agccgacacc cattctttt                      30
```

<210> SEQ ID NO 59
<211> LENGTH: 34
<212> TYPE: DNA
<213> ORGANISM: Artificial Sequence
<220> FEATURE:
<223> OTHER INFORMATION: Probe sequence for the ITS2 locus in Candida
      albicans

<400> SEQUENCE: 59

```
tttttttttg aaagacggta gtggtaagtt tttt               34
```

<210> SEQ ID NO 60
<211> LENGTH: 34
<212> TYPE: DNA
<213> ORGANISM: Artificial Sequence
<220> FEATURE:
<223> OTHER INFORMATION: Probe sequence for the ITS2 locus in Candida
      spp. Group 1

<400> SEQUENCE: 60

```
tttttttgtt tggtgttgag cratacgtat tttt               34
```

```
<210> SEQ ID NO 61
<211> LENGTH: 35
<212> TYPE: DNA
<213> ORGANISM: Artificial Sequence
<220> FEATURE:
<223> OTHER INFORMATION: Probe sequence for the ITS2 locus in Candida
      spp. Group 2

<400> SEQUENCE: 61
ttttactgtt tggtaatgag tgatactctc atttt                                35
```

METHOD FOR IDENTIFYING MASTITIS-CAUSING MICROBES

CROSS-REFERENCE TO RELATED APPLICATIONS

This non-provisional application claims benefit of priority under 35 U.S.C. § 119(e) of provisional application U.S. Ser. No. 62/928,899, filed Oct. 31, 2019, the entirety of which is hereby incorporated by reference.

BACKGROUND OF THE INVENTION

Field of the Invention

The present invention relates to the fields of bovine diseases and microarray technology for microbe identification. More specifically, the present invention relates to raw milk sample preparation and a high throughput method of microarray identification of the microbes therein.

Description of the Related Art

Bovine mastitis, a mammary gland infection caused by microbes, is the most common disease in dairy cattle. The microbes cause a persistent, inflammatory reaction of the udder tissue which is potentially fatal. The infection may be clinical, which is readily apparent from sudden onset, alterations in milk composition and appearance or sub-clinical which has no visible signs on the udder or in the milk.

The California mastitis test (CMT) has been used to screen for sub-clinical mastitis. Samples from raw, untreated whole milk are immediately cultured on standard bacterial media or stored at 4° C. until cultured. Identification of bacteria growing on the media can then be made.

Lima et al. (1) describe how microbes may be collected as part of a "casein pellet" upon simple benchtop 16,000×g microfuge centrifugation of whole milk, followed by lysis of the microbes in the pellet and DNA purification and next generation sequencing (NGS) PCR and deep NGS resequencing to obtain full speciation. Lima et al. state that the microbial complement obtained via centrifugal recovery of their "casein pellet" is identical to that obtained from DNA extraction from the entire whole milk fraction prior to centrifugation. However, although not shown explicitly in the reference, with the relatively low speed centrifugation used 16,000×g it is predicted that very little of the total casein nanoparticle "micelle" fraction contained in the whole milk is collected. Consistent with that observation, Bicalho et al. do not explicitly remove casein from the resulting microbial pellet, other than to rinse the pellet with PBS.

Thus, there is a need in the art for improved collection from and identification of the microbial complement present in a milk sample. More particularly, there is a need for a method for obtaining mastitis-causing microbes from a raw milk sample, including from the fat layer, via centrifugal pelleting with subsequent microarray analysis and identification of the microbes. The present invention fulfills this longstanding need and desire in the art.

SUMMARY OF THE INVENTION

The present invention is directed to a method for identifying a mastitis-causing microbe in a subject. In the method a milk sample is obtained from the subject and the milk sample is centrifuged twice to separate a microbial pellet from the milk sample. Total nucleic acids comprising DNA and non-DNA nucleic acids are extracted from the pellet and a microarray analysis of the DNA extracted from the pellet is performed. The mastitis-causing microbe is identified from hybridization of the DNA to mastitis-causing microbe species specific gene probes at specific known positions on the microarray.

The present invention is directed to a related method for identifying further comprising emulsifying a fat complement of the milk sample prior to the centrifuging step. The present invention is directed to another related method for identifying further comprising identifying a drug resistant mastitis-causing microbe from hybridization of the DNA to a microbial species-specific drug resistance gene.

The present invention also is directed to a method for diagnosing a bovine mastitis infection in a dairy cow. In the method a raw milk sample is obtained from the dairy cow and the milk sample is centrifuged twice to separate a microbial pellet from the raw milk sample. Total nucleic acids comprising DNA and non-DNA nucleic acids are isolated from the pellet. The microbial DNA in the total nucleic acids is amplified with at least one primer pair selective for at least one bovine mastitis-causing microbe-specific DNA to yield at least one bovine mastitis-causing microbe-specific amplicons. The bovine mastitis-causing microbe-specific amplicons as templates are amplified with at least one fluorescent labeled primer pair to yield fluorescent labeled amplicons. The fluorescent labeled amplicons are hybridized with the mastitis-causing microbe species-specific gene probes immobilized at specific known positions on the microarray. The microarray is imaged to detect fluorescent signals from the hybridized fluorescent-labeled amplicons at the specific known positions and the position of the fluorescent signals on the microarray correlates to a presence of the specific bovine mastitis-causing microbe in the raw milk, thereby diagnosing the bovine mastitis infection in the dairy cow.

The present invention is directed to a related method of diagnosing further comprising emulsifying a fat complement of the milk sample prior to the centrifuging step. The present invention is directed to another related method of diagnosing further comprising diagnosing drug resistance in the bovine mastitis-causing microbe from hybridization of the DNA to a microbial species-specific drug resistance gene.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

(FIG. 1A) and 25° C. (FIG. 1B) without centrifugation.

(FIG. 7A), 25° C. (FIG. 7B), 37° C. (FIG. 7C), each for 15 mins before centrifugation at 16,000×g.

FIGS. 8A-8C compare growth on TSA plates of the fat, skim and pellet fractions from Golden Rule (F) raw milk after 48 hrs at 37° C. with incubation at 4° C. (FIG. 8A), 25° C. (FIG. 8B), 37° C. (FIG. 8C), each for 15 mins before centrifugation at 16,000×g.

DETAILED DESCRIPTION OF THE INVENTION

Figures 1A, 1B:
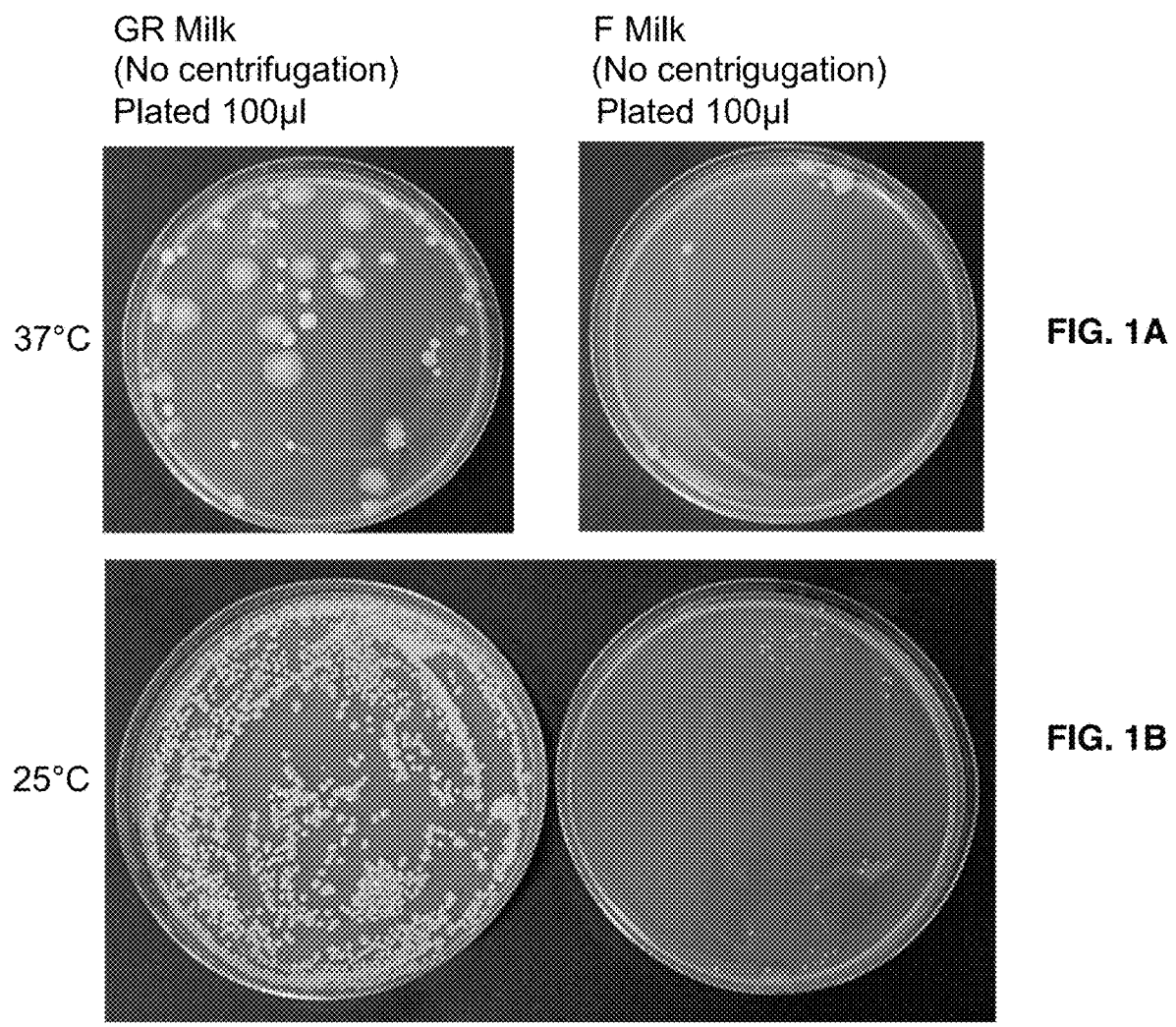
FIGS. 1A-1B show growth on TSA plates of Golden Rule (G) and Fond du Lac (F) raw milk samples after 48 hrs at 37° C.
Figure 2A:
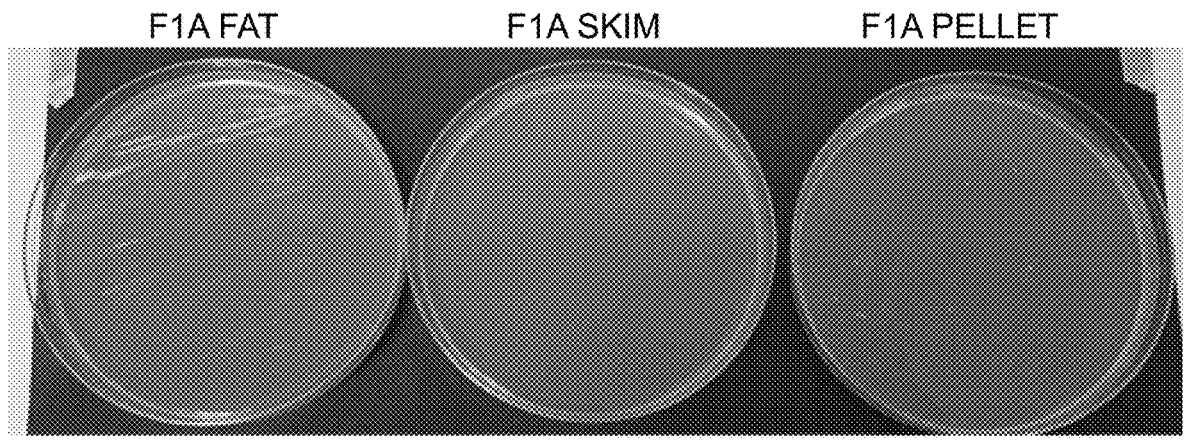
FIGS. 2A-2B show growth on TSA plates of the fat, skim and pellet fractions from Fond du Lac (F) raw milk after 48 hrs at 25° C. with incubation at 4° C. for 15 mins before centrifugation at 8,000×g (FIG. 2A) and 16,000×g (FIG. 2B).
Figure 2B:
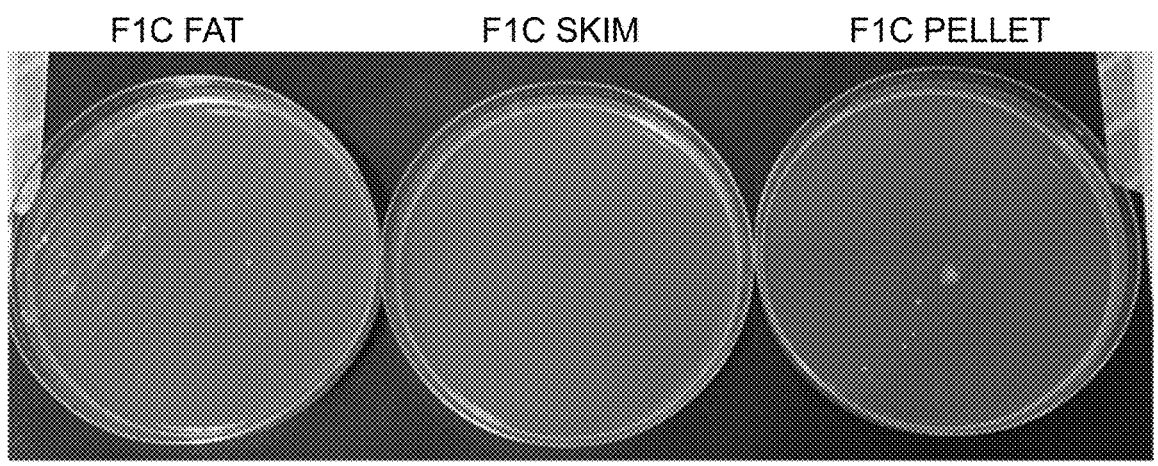
Figure 3A:
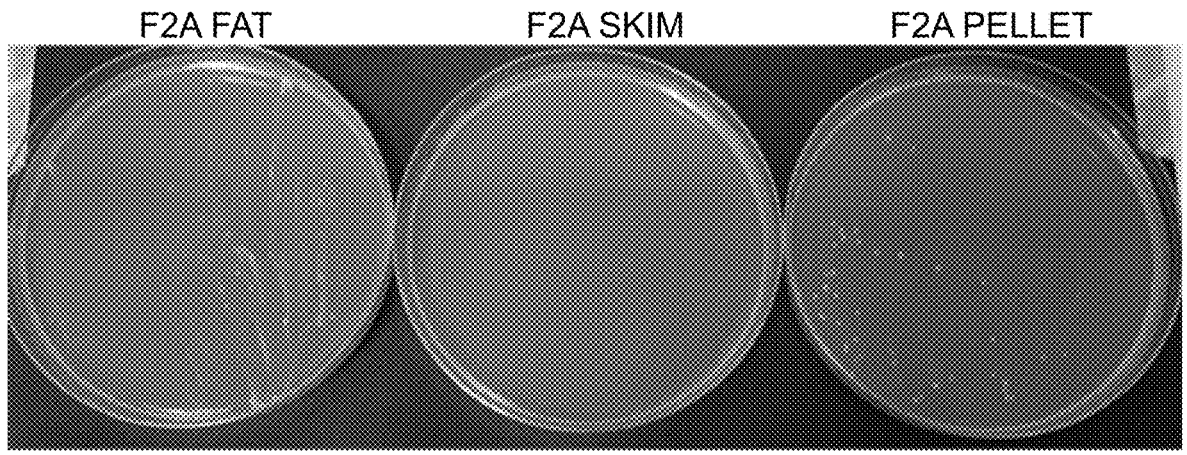
FIGS. 3A-3B show growth on TSA plates of the fat, skim and pellet fractions from Fond du Lac (F) raw milk after 48 hrs at 25° C. with incubation at 25° C. for 15 mins before centrifugation at 8,000×g (FIG. 3A) and 16,000×g (FIG. 3B).
Figure 3B:
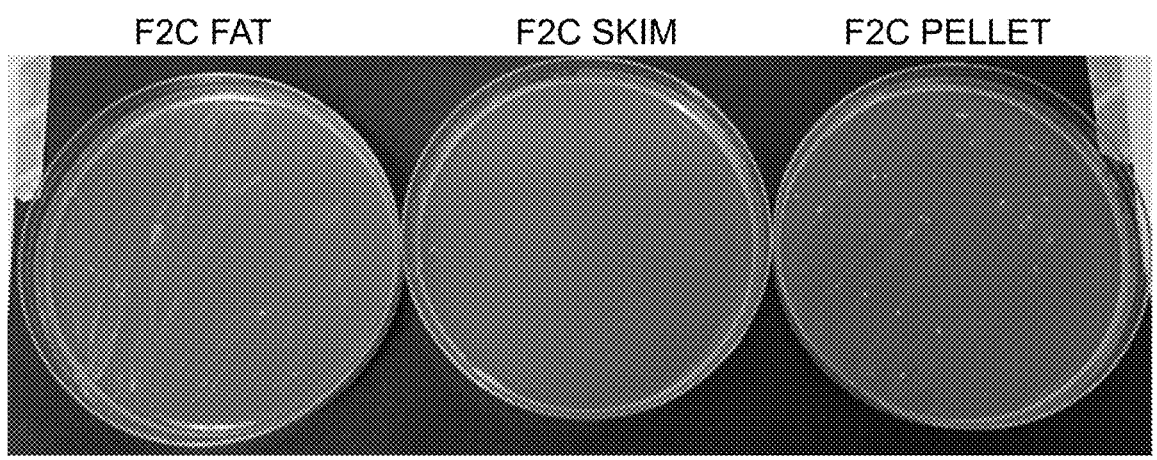
Figure 4A:
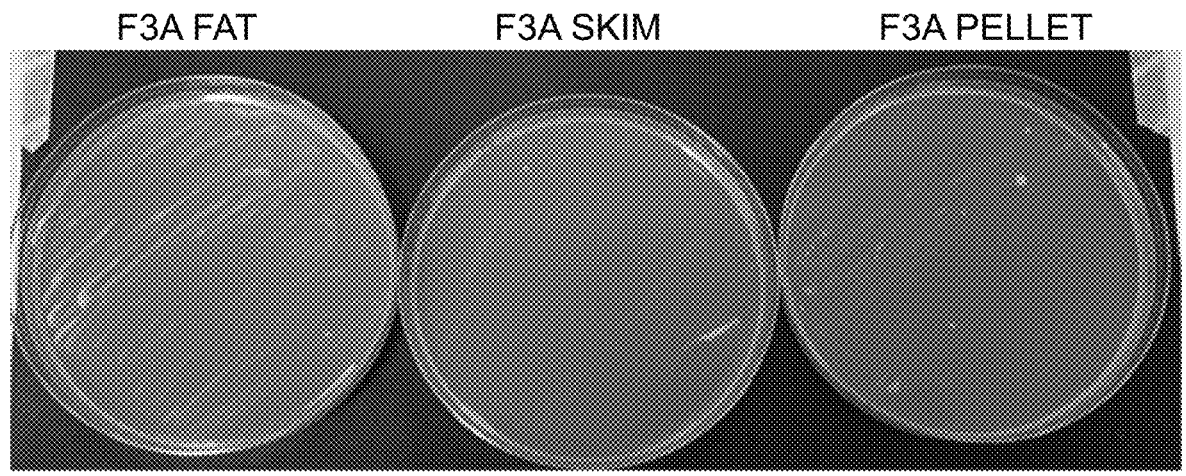
FIGS. 4A-4B show growth on TSA plates of the fat, skim and pellet fractions from Fond du Lac (F) raw milk after 48 hrs at 25° C. with incubation at 37° C. for 15 mins before centrifugation at 8,000×g (FIG. 4A) and 16,000×g (FIG. 4B).
Figure 4B:
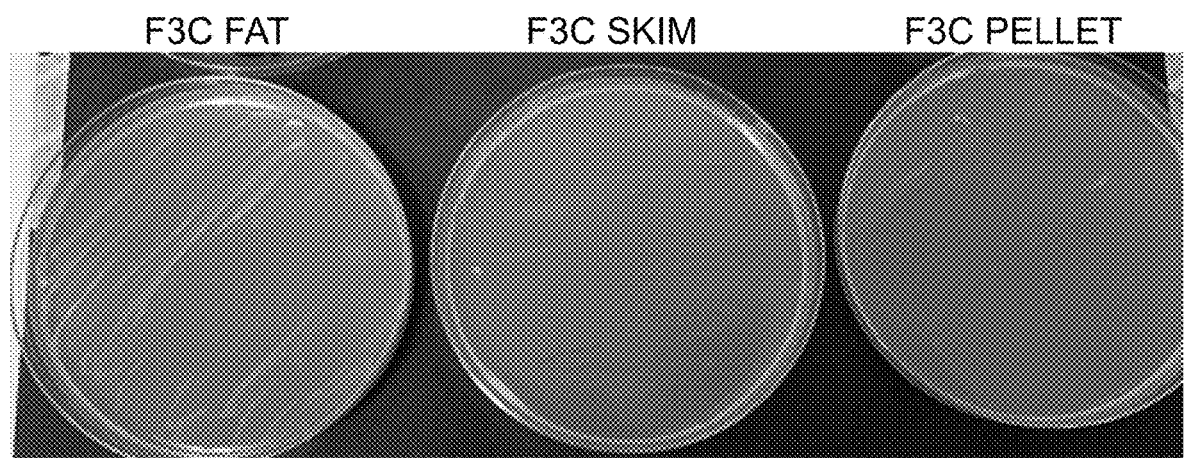
Figure 5A:
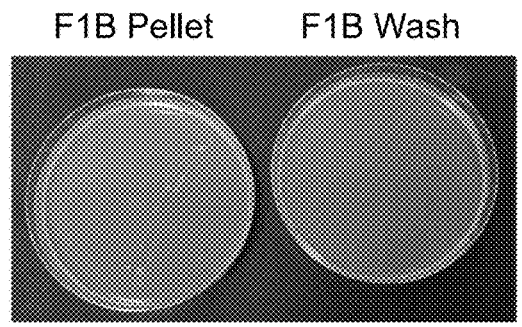
FIGS. 5A-5F show growth on TSA plates of the pellet fraction and wash from Fond du Lac (F) raw milk after 48 hrs at 25° C. with incubation at 4° C., 25° C. and 37° C. for 15 mins before centrifugation at 8,000×g (FIGS. 5A-5C) and 16,000×g (FIGS. 5D-5F).
Figure 5B:
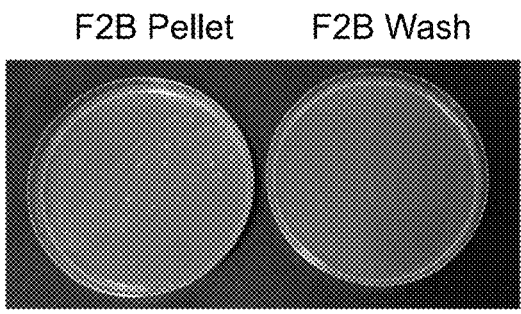
Figure 5C:
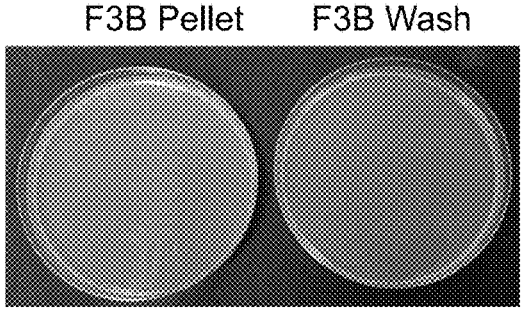
Figure 5D:
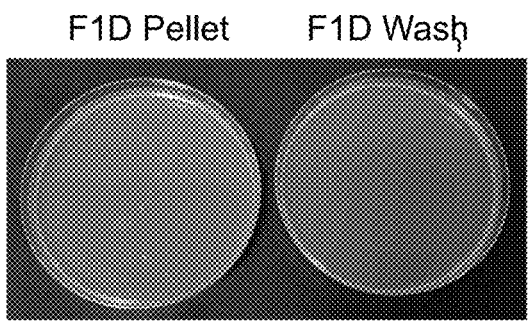
Figure 5E:
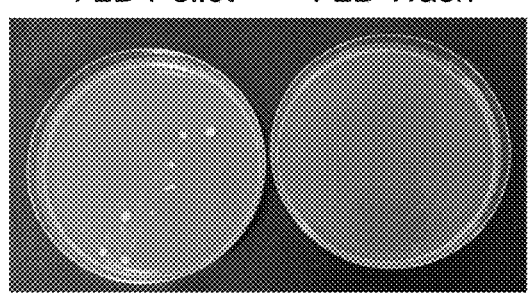
Figure 5F:
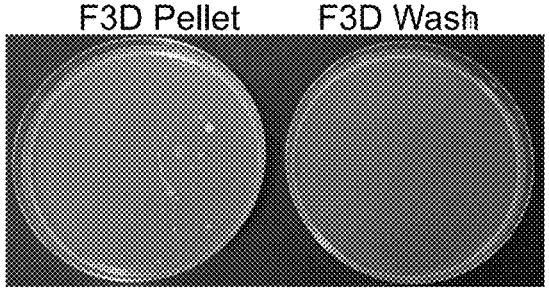

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein the terms "casein micelles" and "casein nanoparticles" are interchangeable and refer to the solid, porous structures in milk of about 100 nm to about 200 nm in diameter in which casein is sequestered and stabilized by discrete paracrystalline clusters of calcium phosphate distributed within the nanoparticle volume.

As used herein the terms "fat", "fat layer" and "fat globules" are interchangeable and refer to the raw milk complement that exists as a suspension of fluid milk fat micelles in the water phase presented by skim milk as the supporting solvent phase In one embodiment of the present invention there is provided a method for identifying a mastitis-causing microbe in a subject, comprising the steps of obtaining a milk sample from the subject; centrifuging the milk sample twice to separate a microbial pellet from the milk sample; extracting total nucleic acids comprising DNA and non-DNA nucleic acids from the pellet; performing a microarray analysis of the DNA extracted from the pellet; and identifying the mastitis-causing microbe from hybridization of the DNA to mastitis-causing microbe species-specific gene probes at specific known positions on the microarray.

Further to this embodiment the method comprises emulsifying a fat complement of the milk sample prior to the centrifuging step. In another further embodiment the method comprises identifying a drug resistant mastitis-causing microbe from hybridization of the DNA to a microbial species-specific drug resistance gene. In an aspect of this embodiment the microbial species-specific drug resistance gene is a beta-lactamase gene. Particularly, the microbial species-specific drug resistance gene is a *Staphylococcus* beta-lactamase gene.

In one aspect of all embodiments the step of centrifuging the milk sample may be performed at a centrifuging speed of about 400×g to about 16,000×g. In this aspect a first centrifuging speed may be about 400×g and a second centrifuging speed may be about 8,000×g.

In another aspect of all embodiments the extracting step may comprise lysing the microbial pellet and then treating with an enzyme. In yet another aspect the step of performing microarray analysis may comprises amplifying the microbial DNA in the total nucleic acids with at least one primer pair selective for at least one mastitis-causing microbe-specific DNA to yield at least one mastitis-causing microbe-specific amplicons; amplifying the mastitis-causing microbe-specific amplicons as templates with at least one fluorescent labeled primer pair to yield fluorescent-labeled amplicons; and hybridizing the fluorescent labeled amplicons with the mastitis-causing microbe species-specific gene probes on the microarray.

In all embodiments and aspects thereof the mastitis-causing microbe species specific gene probes may be DNA sequences or partial DNA sequences of the mastitis-causing microbes to be identified or DNA sequences complementary or homologous thereto. Also in all embodiments and aspects a detectable concentration of the microbe in the milk sample is about $10^2$ CFU/ml.

In addition the mastitis-causing microbe may be a bacterium, a fungus, or an algae. In one aspect the bacterium may be *Staphylococcus aureus, Streptococcus agalactiae, Streptococcus dysgalactiae, Streptococcus uberis, Enterococcus faecalis, Enterococcus faecium, Corynebacterium bovis, Trueperella pyogenes, Peptoniphilus indolicus, Arcanobacterium pyogenes, Escherichia coli, Klebsiella oxytoca, Klebsiella pneumoniae, Serratia marcescens, Mycoplasma bovis, Mycoplasma alkalescens, Mycoplasma bovigenitalium, Mycoplasma canadense, Mycoplasma californicum*, and *Mannheimia haemolitica*. In another aspect the fungus may be *Aspergillus fumigatus* or a *Candida* spp. In yet another aspect the algae may be a *Prototheca* spp.

In another embodiment of the present invention there is provided a method for diagnosing a bovine mastitis infection in a dairy cow, comprising the steps of obtaining a raw milk sample from the dairy cow; centrifuging the milk sample twice to separate a microbial pellet from the raw milk sample; isolating total nucleic acids from the pellet comprising DNA and non-DNA nucleic acids; amplifying the microbial DNA in the total nucleic acids with at least one primer pair selective for at least one bovine mastitis-causing microbe-specific DNA to yield at least one bovine mastitis-causing microbe-specific amplicons; amplifying the bovine mastitis-causing microbe-specific amplicons as templates with at least one fluorescent labeled primer pair to yield fluorescent-labeled amplicons; hybridizing the fluorescent-labeled amplicons with the mastitis-causing microbe species-specific gene probes immobilized at specific known positions on the microarray; imaging the microarray to detect fluorescent signals from the hybridized fluorescent-labeled amplicons at the specific known positions; and correlating the position of the fluorescent signals on the microarray to a presence of the specific bovine mastitis-causing microbe in the raw milk, thereby diagnosing the bovine mastitis infection in the dairy cow.

Further to this embodiment the method comprises emulsifying a fat complement of the raw milk sample prior to the centrifuging step. In another further embodiment the method comprises diagnosing drug resistance in the bovine mastitis-causing microbe from hybridization of the DNA to a microbial species-specific drug resistance gene. In this further embodiment the microbial species specific drug resistance gene is a beta-lactamase gene.

In all embodiments a first centrifuging speed may be about 400×g and a second centrifuging speed is about 8,000×g. Also in all embodiments the bovine mastitis-causing microbe species specific gene probes may be DNA sequences or partial DNA sequences of the mastitis-causing microbes to be identified or DNA sequences complementary or homologous thereto. In addition a detectable concentration of the bovine mastitis-causing microbe in the raw milk sample is about $10^2$ CFU/ml.

In one aspect of all embodiments the bovine mastitis-causing microbe is a bacterium Staphylococcus aureus, Streptococcus agalactiae, Streptococcus dysgalactiae, Streptococcus uberis, Enterococcus faecalis, Enterococcus faecium, Corynebacterium bovis, Trueperella pyogenes, Peptoniphilus indolicus, Arcanobacterium pyogenes, Escherichia coli, Klebsiella oxytoca, Klebsiella pneumoniae, Serratia marcescens, Mycoplasma bovis, Mycoplasma alkalescens, Mycoplasma bovigenitalium, Mycoplasma canadense, Mycoplasma californicum, and Mannheimia haemolitica. In another aspect the bovine mastitis-causing microbe may be a fungus Aspergillus fumigatus or a Candida spp. In yet another aspect the bovine mastitis-causing microbe is an algae of a Prototheca spp.

Provided herein are methods to isolate and identify mastitis-causing microbes, such as, but not limited to, pathogenic bacteria, fungi, and algae, present in raw milk. Generally a pellet containing the microbes is obtained via centrifugation, total nucleic acids isolated therefrom, DNA or RNA of interest amplified without the necessity of prior purification and the microbe identified via hybridization of the amplicons to probes on a microarray. The method can detect as few as about $10^2$ CFU in the pellet.

Moreover, it is demonstrated that during sample preparation after centrifugation, there are microbes present in both the pellet and the fat layer, but not the skim layer. However, emulsifying the fat layer prior to centrifugation may render the microbes contained therein more pelletable or accessible for subsequent hybridization.

Also provided is a method of diagnosing mastitis bovine mastitis based on the identification of the mastitis-causing microbe in the whole milk or raw milk sample. Because identification is based on as few as $10^2$ CFU/ml microbes both sub-clinical and clinical cases of the disease may be diagnosed.

In addition there is provided methods to determine drug resistance, such as penicillin-resistance, in the identified mastitis-causing microbes. The microarray also may contain a probe to detect drug resistance, such as, but not limited to, resistance conferred by the presence of a beta-lactamase gene indicative of penicillin-resistance. A non-limiting example is a Staphylococcus beta-lactamase gene.

The microarray or mastitis chip may identify gram positive Staphylococcus spp., including all major coagulase-negative staphylococci, Streptococcus spp. and Enterococcus spp. Non-limiting examples are Staphylococcus aureus, Streptococcus agalactiae, Streptococcus dysgalactiae, Streptococcus uberis, Enterococcus faecalis, Enterococcus faecium, Corynebacterium bovis, Trueperella pyogenes, Peptoniphilus indolicus, and Arcanobacterium pyogenes.

The mastitis chip may identify gram negative bacteria, including Pseudomonas spp., Mycoplasma spp. and pathogenic Enterobacteriaceae. Non-limiting examples are Escherichia coli, Klebsiella oxytoca, Klebsiella pneumoniae, Serratia marcescens, Mycoplasma bovis, Mycoplasma alkalescens, Mycoplasma bovigenitalium, Mycoplasma canadense, Mycoplasma californicum, and Mannheimia haemolytica.

The mastitis chip may identify fungal and algal causes of mastitis. Non-limiting examples of these pathogenic microbes are the mold Aspergillus fumigatus, yeast, such as Candida spp. and the Prototheca spp. of algae.

The mastitis chip or microarray may comprise probes generic for at least one mastitis-causing microbial species or specific for at least one particular mastitis-causing microbe. The probes may differentiate between gram positive and gram negative pathogens, may differentiate among bacteria, fungi and algae and may identify resistance. The probes may comprise DNA sequences or partial DNA sequences of the mastitis-causing microbes to be identified or DNA sequences complementary or homologous thereto.

Generally, the probes are immobilized at specific locations on the microarray or the mastitis chip. Fluorescent labeled amplicons generated from DNA in the total nucleic acids isolated from the whole or raw milk sample in a two step amplification are hybridized to the probes. A detectable fluorescent signal, for example, via imaging of the microarray, at a specific location on the microarray or mastitis chip identifies the mastitis-causing microbe species or specific mastitis-causing microbe. In a first PCR amplification the microbial DNA in the total nucleic acids are amplified with at least one primer pair selective for at least one mastitis-causing microbe-specific DNA to yield, produce or generate at least one mastitis-causing microbe-specific amplicons. These amplicons provide templates for a second PCR amplification with at least one fluorescent labeled primer pair to yield, produce or generate fluorescent labeled amplicons for subsequent hybridization.

The following examples are given for the purpose of illustrating various embodiments of the invention and are not meant to limit the present invention in any fashion.

EXAMPLE 1

Methods and Materials
Raw Milk

Whole Raw Jersey Milk (Golden Rule Dairy) and Fond du Lac Farms Raw Milk were purchased from Aqua Vita Market (Tuscan, Arizona).

Culture Media

Microbes were cultured on trypticase soy agar (TSA) plates.

Mastitis Chip

The mastitis chip is a microarray of hybridization probes to detect at least one mastitis-causing pathogenic microbe and the presence of a beta-lactamase or other drug resistance marker.

Protocol to Establish Raw Milk Sample Temperature Prior to Centrifugation and Centrifuge Speed 1) Obtain raw milk and store at 4° C. When ready to use, invert back and forth 15 times to homogenize. Fond du Lac Farms (F) raw milk and Golden Rule Dairy (G) whole raw milk are used.
2) Transfer 1 mL samples of raw milk to 1.7 mL tubes and centrifuge as shown in Table 1:

TABLE 1

| Sample ID | Temperature/Time | Centrifuge Conditions |
|---|---|---|
| F1A & F1B | 4° C. for 15 mins | 8,000xg for 5 mins |
| F1C & F1D | 4° C. for 15 mins | 16,000xg for 5 mins |
| F2A & F2B | Room temp (25° C.) for 15 mins | 8,000xg for 5 mins |
| F2C & F2D | Room temp (25° C.) for 15 mins | 16,000xg for 5 mins |
| F3A & F3B | 37° C. for 15 mins | 8,000xg for 5 mins |
| F3C & F3D | 37° C. for 15 mins | 16,000xg for 5 mins |

3) Remove the fat layer and place in a new tube for the A and C samples.
4) Remove the skim milk layer from below the fat layer.
5) Pipet the skim milk layer into a new tube for tubes A and C only.
6) The original tube should contain the bacteria pellet.
7) To tubes B and D only:
   Pipet out the fat and skim milk layer and discard.
   Add 1 mL of molecular biology Grade 1×PBS.
   Gently vortex (setting 5) for 10 seconds.
   Centrifuge at 8,000×g for the B tubes and 16,000×g for the D tubes to remove residual fat and protein.
   Remove the 1×PBS via pipet and transfer to a new 1.7 mL tube.
8) Pipette 100 μl of each fraction onto TSA plates: Fat layer (top layer), skim milk layer (middle layer), pellet (bottom of tube) and 100 μl of the raw milk (no centrifugation) onto 2 TSA plates.
9) Incubate at 37° C. and 25° C. for 24-48 hrs and check for microbial growth.

Protocol to Establish Distribution of Microbes in Raw Milk Fractions after Centrifugation 1) Obtain raw milk and store at 4 C. When ready to use, invert back and forth 15 times to homogenize. Fond du Lac (F) raw milk and Golden Rule Farms (G) raw whole milk are used. Golden Rule milk had quite a few fat globules in the milk. Inverting 15 times to homogenize did not break up the fat globules.
2) Transfer 1 mL samples of raw milk to 1.7 mL tubes and centrifuge as shown in Table 2.

TABLE 2

| Sample ID | Condition prior to centrifugation |
|---|---|
| F1 & G1 | 4° C. for 15 mins |
| F2 & G2 | Room temp (25° C.) for 15 mins |
| F3 & G3 | 37° C. for 15 mins |

3) Centrifuge each tube after the 15 minute incubation at the listed temperature for 5 minutes at 2500×g.
4) Remove the skim milk layer (below the fat layer), and transfer to a new tube, leaving the fat layer behind.
5) Centrifuge the skim milk (which should contain the bacterial cells) at 16,000×g for 5 minutes.
6) Transfer the skim milk layer (avoid the pellet) to another tube.
7) Plate each fraction on TSA: Fat layer (top layer), skim milk layer (middle layer), pellet (bottom of tube).
   Transfer a loopful to each plate and spread as evenly as possible. Include a plate for each milk type with raw milk having no centrifugation.
   Incubate at 37° C. and 25° C. for 24-48 hrs and check for microbial growth.

Whole Milk Processing for High-Throughput Screening on a Mastitis Chip

1) Pipette 1 ml of whole milk or raw milk into a 2 ml screw cap microfuge tube. The raw milk sample may be homogenized and/or the fat globules emulsified prior to centrifugation.
2) Spin at 400 g for 10 min on a benchtop microfuge (4° C. cooling is optional) to separate fat and pellet lymphocytes. Remove the skim milk phase by pipetting. Take care not to dislodge the lymphocyte pellet.
3) Spin at 8,000 g for 5 min on a benchtop microfuge (4° C. cooling is optional).
4) Gently remove the fluid over the pellet and discard the upper skim milk phase by decanting the combined fluid phase or by pipetting.
5) Wash the resulting microbial pellet which remains with 1 ml PBS (gentle vortex or pipette mixing) and spin a second time at 8,000 g to wash off residual fat and milk protein. If needed, alternatively, the resulting washed pellet is suspended in 1 ml of Tris-EDTA buffer, mixed and incubated at room temperature for 5 min. This Tris-EDTA soaking step quickly chelates calcium from the casein nanoparticle (micelles) and dissociates the casein nanoparticles into unstable microclusters, which can then be removed into the supernatant obtained after a second 8,000 g spin.
6) Lyse and enzyme treat the resulting microbial pellet to isolate total nucleic acids, DNA and non-DNA nucleic acids.
7) Perform microarray analysis.

Procedure for Microarray Analysis of Pelleted Microbes

Amplification

1) Amplify the DNA with one or more PCR primers specific for a region of one or more microbes in a first amplification. The primers contain
2) Amplify about 1 μL of the amplicons from the first amplification to additionally amplify and label the first amplicons with a fluorophore, such as, but not limited to, CY3 or CY5 fluorescent labels in a second amplification.
3) Dilute the labeled second amplicons 1-1 with 4×SSC+ 5×Denhardt's solution hybridization buffer.

TABLE 3

| Primer sequences for PCR amplification | | |
|---|---|---|
| SEQ ID NO. | Primer target | Primer sequence |
| First PCR Primers for the first amplification step | | |
| SEQ ID NO: 1 | 16s rDNA HV3 Locus (Bacteria) | TTTCACAYTGGRACTGA GACACG |
| SEQ ID NO: 2 | 16s rDNA HV3 Locus (Bacteria) | TTTGACTACCAGGGTAT CTAATCCTGT |

TABLE 3-continued

Primer sequences for PCR amplification

| SEQ ID NO. | Primer target | Primer sequence |
|---|---|---|
| SEQ ID NO: 3 | Stx1 Locus (Pathogenic E. coli) | TTTATAATCTACGGCTT ATTGTTGAACG |
| SEQ ID NO: 4 | Stx1 Locus (Pathogenic E. coli) | TTTGGTATAGCTACTGT CACCAGACAATG |
| SEQ ID NO: 5 | Stx2 Locus (Pathogenic E. coli) | TTTGATGCATCCAGAGC AGTTCTGCG |
| SEQ ID NO: 6 | Stx2 Locus (Pathogenic E. coli) | TTTGTGAGGTCCACGTC TCCCGGCGTC |
| SEQ ID NO: 7 | tuf Locus (All E. coli) | TTTCAGAGTGGGAAGCG AAAATCCTG |
| SEQ ID NO: 8 | tuf Locus (All E. coli) | TTTACGCCAGTACAGGT AGACTTCTG |
| SEQ ID NO: 9 | 16s rDNA Enterobacteriaceae HV3 Locus | TTACCTTCGGGCCTCTT GCCATCRGATGTG |
| SEQ ID NO: 10 | 16s rDNA Enterobacteriaceae HV3 Locus | TTGGAATTCTACCCCCC TCTACRAGACTCAAGC |
| SEQ ID NO: 11 | ITS2 Locus (All Yeast, Mold/Fungus) | TTTACTTTYAACAAYGG ATCTCTTGG |
| SEQ ID NO: 12 | ITS2 Locus (All Yeast, Mold/Fungus) | TTTCTTTTCCTCCGCTT ATTGATATG |
| SEQ ID NO: 13 | ITS2 Locus (Aspergillus species) | TTTAAAGGCAGCGGCGG CACCGCGTCCG |
| SEQ ID NO: 14 | ITS2 Locus (Aspergillus species) | TTTTCTTTTCCTCCGCT TATTGATATG |

Second PCR Primers (P2) for the second labeling amplification step

| SEQ ID NO. | Primer target | Primer sequence |
|---|---|---|
| SEQ ID NO: 15 | 16s rDNA HV3 Locus (All Bacteria) | TTTACTGAGACACGGYC CARACTC |
| SEQ ID NO: 16 | 16s rDNA HV3 Locus (All Bacteria) | TTTGTATTACCGCGGCT GCTGGCA |
| SEQ ID NO: 17 | Stx1 Locus (Pathogenic E. coli) | TTTATGTGACAGGATTT GTTAACAGGAC |
| SEQ ID NO: 18 | Stx1 Locus (Pathogenic E. coli) | TTTCTGTCACCAGACAA TGTAACCGCTG |
| SEQ ID NO: 19 | Stx2 Locus (Pathogenic E. coli) | TTTTGTCACTGTCACAG CAGAAG |
| SEQ ID NO: 20 | Stx2 Locus (Pathogenic E. coli) | TTTGCGTCATCGTATAC ACAGGAGC |
| SEQ ID NO: 21 | tuf Locus (All E. coli) | TTTGTTGTTACCGGTCG TGTAGAAC |
| SEQ ID NO: 22 | tuf Locus (All E. coli) | TTTCTTCTGAGTCTCTT TGATACCAACG |
| SEQ ID NO: 23 | 16s rDNA Enterobacteriaceae HV3 Locus | TTATATTGCACAATGGG CGCAAGCCTGATG |
| SEQ ID NO: 24 | 16s rDNA Enterobacteriaceae HV3 Locus | TTTTGTATTACCGCGGC TGCTGGCA |
| SEQ ID NO: 25 | ITS2 Locus (All Yeast, Mold/Fungus) | TTTGCATCGATGAAGAR CGYAGC |
| SEQ ID NO: 26 | ITS2 Locus (All Yeast, Mold/Fungus) | TTTCCTCCGCTTATTGA TATGC |
| SEQ ID NO: 27 | ITS2 Locus (Aspergillus species) | TTTCCTCGAGCGTATGG GGCTTTGTC |
| SEQ ID NO: 28 | ITS2 Locus (Aspergillus species) | TITTTCCTCCGCTTATI GATATGC |
| SEQ ID NO: 29 | Fungal RSG Primers (All Fungus) | TTTACTTTCAACAAYGG ATCTCTTGG |
| SEQ ID NO: 30 | Fungal RSG Primers (All Fungus) | CTTTTCCTCCGCTTATT GATATG |
| SEQ ID NO: 31 | Bacterial RSG Primers (All Bacteria) | TTTCACACTGGRACTGA GACACG |
| SEQ ID NO: 32 | Bacterial RSG Primers (All Bacteria) | TTTTGTATTACCGCGGC TGCTGGC |
| SEQ ID NO: 33 | Fungal Labeling Primers (All Fungus) | TTTGCATCGATGAAGAA CGCAGC |
| SEQ ID NO: 34 | Fungal Labeling Primers (All Fungus) | TTTTCCTCCGCTTATTG ATATGC |
| SEQ ID NO: 35 | Bacterial Labeling Primers | TTTCACACTGGRACTGA GACACGG |

Hybridization

Probe sequences may be indirectly linked by photocrosslinking to an activated surface, for example, an epoxysilane surface, on a glass substrate, such as, borosilicate glass microarray substrate, via a fluorescent labeled (CY5) bifunctional polymeric linker, for example, an oligonucleotide thymidine linker (OligoT) covalently bound thereto.

1) Pipette the labeled second amplicons+hybridization buffer onto the microarray comprising probe sequences complementary to the amplified regions in the microbes. The probe sequences also may comprises at least one drug resistance gene.

2) Incubate for 30 minutes to allow DNA binding to the microarray (typically at room temperature, RT).
3) Remove the DNA+ binding buffer by pipetting.
4) Pipette 50 uL of wash buffer onto the microarray (0.4×SSC+0.5×Denhardt's) and incubate 5 min at RT.
5) Remove the wash buffer by pipetting.
6) Repeat steps 4 and 5.
7) Perform image analysis at 532 nm and 635 nm to detect the probe spot location (532 nm) and PCR product hybridization (635 nm). Overlaying the resultant images identifies the microbe and can identify drug resistance. Image analysis may be performed on a raster-based confocal scanner (GenePix 4000B Microarray Scanner).

TABLE 4

Oligonucleotide probe sequence for the 16S Locus

| | | |
|---|---|---|
| SEQ ID NO: 36 | Total Aerobic bacteria (High) | TTTTTTTTCCTACGGGAGGCAGTTTTTTT |
| SEQ ID NO: 37 | Total Aerobic bacteria (Medium) | TTTTTTTTCCCTACGGGAGGCATTTTTTT |
| SEQ ID NO: 38 | Total Aerobic bacteria (Low) | TTTATTTTCCCTACGGGAGGCTTTTATTT |
| SEQ ID NO: 39 | Enterobacteriaceae (Low sensitivity) | TTTATTCTATTGACGTTACCCATTTATTT |
| SEQ ID NO: 40 | Enterobacteriaceae (medium sensitivity) | TTTTTTCTATTGACGTTACCCGTTTTTTT |
| SEQ ID NO: 41 | *Escherichia coli* | TTTTCTAATACCTTTGCTCATTGACTCTTT |
| SEQ ID NO: 42 | *Escherichia coli* | TTTTTTAAGGGAGTAAAGTTAATATTTTTT |
| SEQ ID NO: 43 | *Escherichia coli* | TTTTCTCCTTTGCTCATTGACGTTATTTTT |
| SEQ ID NO: 44 | Bile-tolerant Gram-negative (High) | TTTTTCTATGCAGTCATGCTGTGTGTRTGT CTTTTT |
| SEQ ID NO: 45 | Bile-tolerant Gram-negative (Medium) | TTTTTCTATGCAGCCATGCTGTGTGTRTTT TTTT |
| SEQ ID NO: 46 | Bile-tolerant Gram-negative (Low) | TTTTTCTATGCAGTCATGCTGCGTGTRTTT TTTT |
| SEQ ID NO: 47 | Coliform/Enterobacteriaceae | TTTTTTCTATTGACGTTACCCGCTTTTTTT |
| SEQ ID NO: 48 | etuf gene | TTTTTTCCATCAAAGTTGGTGAAGAATCTT TTTT |
| SEQ ID NO: 49 | *Klebsiella oxytoca* | TTTTTTCTAACCTTATTCATTGATCTTTTT |
| SEQ ID NO: 50 | *Klebsiella pneumoniae* | TTTTTTCTAACCTTGGCGATTGATCTTTTT |
| SEQ ID NO: 51 | *Serratia* spp. | TTTATTCTGTGAACTTAATACGTTCATTTT TATT |
| SEQ ID NO: 52 | *Staphylococcus aureus* 1 | TTTATTTTCATATGTGTAAGTAACTGTTTT ATTT |
| SEQ ID NO: 53 | *Staphylococcus aureus* 2 | TTTTTTCATATGTGTAAGTAACTGTTTTTT |

TABLE 5

Oligonucleotide probe sequence for the ITS2 Locus

| | | |
|---|---|---|
| SEQ ID NO: 54 | Total Yeast and Mold (High sensitivity) | TTTTTTTTGAATCATCGARTCTTTGAACGC ATTTTTT |
| SEQ ID NO: 55 | Total Yeast and Mold (Low sensitivity) | TTTTTTTTGAATCATCGARTCTCCTTTTTT T |
| SEQ ID NO: 56 | Total Yeast and Mold (Medium sensitivity) | TTTTTTTTGAATCATCGARTCTTTGAACGT TTTTTT |
| SEQ ID NO: 57 | *Aspergillus fumigatus* 1 | TTTCTTTTCGACACCCAACTTTATTTCCTT ATTT |

TABLE 5-continued

Oligonucleotide probe sequence for the ITS2 Locus

| | | |
|---|---|---|
| SEQ ID NO: 58 | Aspergillus fumigatus 2 | TTTTTTTGCCAGCCGACACCCATTCTTTTT |
| SEQ ID NO: 59 | Candida albicans | TTTTTTTTTGAAAGACGGTAGTGGTAAGTTTTTT |
| SEQ ID NO: 60 | Candida spp. Group 1 | TTTTTTTGTTTGGTGTTGAGCRATACGTATTTTT |
| SEQ ID NO: 61 | Candida spp. Group 2 | TTTTACTGTTTGGTAATGAGTGATACTCTCATTTT |

EXAMPLE 2

Effect of Incubation Time and Temperature and of Centrifugation Speed on Growth of Microbes from the Pellet, Fat and Skim Fractions 100 µl of the raw milk from Golden Rule Farms (G) and Fond du Lac Farms (F) with no centrifugation were streaked on TSA plates and incubated for 48 hrs at 37° C. and 25° C. (FIGS. 1A-1B). Microbial growth was observed for all samples although Golden Rule Farms raw milk has substantially more growth than Fond du Lac Farms raw milk. The pellet, fat and skim fractions from Fond du Lac Farms raw milk incubated prior to centrifugation at 4° C., 25° C., and 37° C. and centrifuged at 8,000×g or 16,000×g were streaked on TSA plates and checked for microbial growth after 48 hrs at 25° C. (FIGS. 2A-2B, 3A-3B, 4A-4B). Table 6 summarizes the results.

TABLE 6

| | Fond du Lac Farms raw milk | | Growth after 48 hrs on TSA at 25° C. | | |
|---|---|---|---|---|---|
| | Incubation | | | | |
| Sample ID | temp, for 15 mins | Centrifugation Speed × 5 min | Fat fraction | Skim fraction | Pellet fraction |
| F1A | 4° C. | 8,000×g | Yes | No | Yes |
| F1C | 4° C. | 16,000×g | Yes | No | Yes |
| F2A | Room Temp 25° C. | 8,000×g | Yes | No | Yes |
| F2C | Room Temp 25° C. | 16,000×g | Yes | No | Yes |
| F3A | 4° C. | 8,000×g | Yes | Yes (1 CFU) | Yes |
| F3C | 4° C. | 16,000×g | No | No | Yes least growth |

The pellet and 1×PBS wash from Fond du Lac Farms raw milk incubated prior to centrifugation at 4° C., 25° C., and 37° C. and centrifuged at 8,000×g or 16,000×g were streaked on TSA plates and checked for microbial growth after 48 hrs at 25° C. (FIGS. 5A-5F). Growth was observed for all pellet fractions only. Table 7 summarizes the results.

TABLE 7

| | Fond du Lac Farms raw milk | | Growth after 48 hrs on TSA at 25° C. | |
|---|---|---|---|---|
| | Incubation | | | |
| Sample ID | temp, for 15 mins | Centrifugation Speed × 5 min | Pellet fraction | Wash fraction |
| F1A | 4° C. | 8,000×g | Yes | No |
| F1C | 4° C. | 16,000×g | Yes | No |
| F2A | Room Temp 25° C. | 8,000×g | Yes | No |
| F2C | Room Temp 25° C. | 16,000×g | Yes | No |
| F3A | 4° C. | 8,000×g | Yes | Yes (1 CFU) |
| F3C | 4° C. | 16,000×g | No | No |

It does appear there bacteria is present in the fat layer and there is none detectable in the skim milk layer. Emulsifying the fat fraction prior to centrifugation may address this and may eliminate the temperature incubation step prior to centrifugation. The centrifugation speed did not yield any observable differences in growth on the TSA plates.

EXAMPLE 3

Figures 6A, 6B:
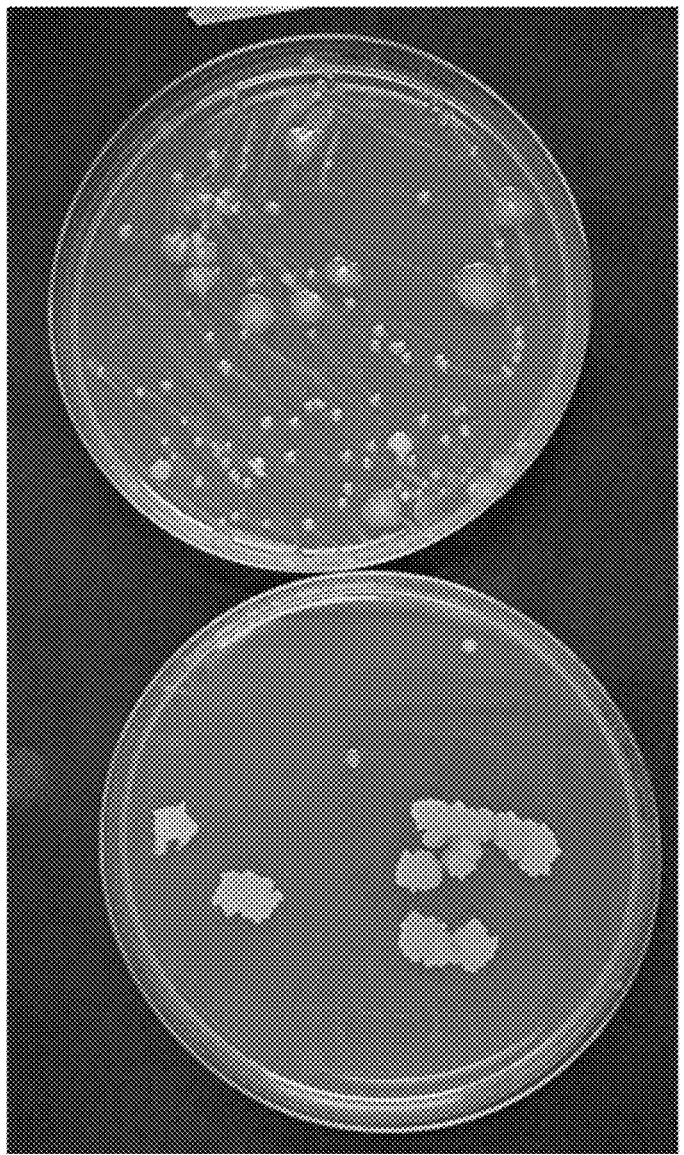
FIGS. 6A-6B show growth on TSA plates of different samples from Fond du Lac (F) (FIG. 6A) and Golden Rule (G) (FIG. 6B) raw milk after 48 hrs at 37° C.
Figure 7A:
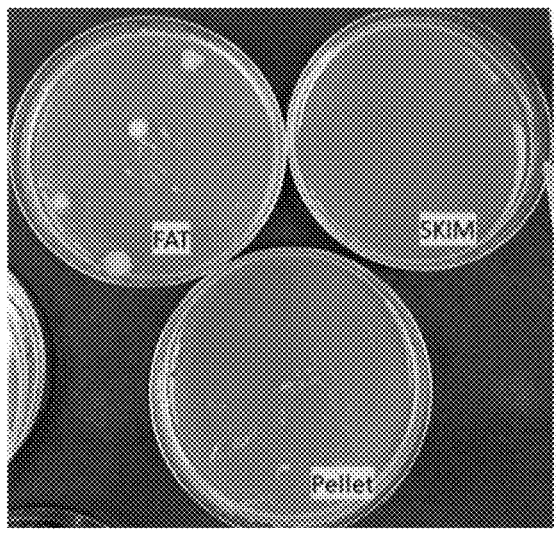
FIGS. 7A-7C compare growth on TSA plates of the fat, skim and pellet fractions from Fond du Lac (F) raw milk after 48 hrs at 37° C. with incubation at 4° C.
Figure 7B:
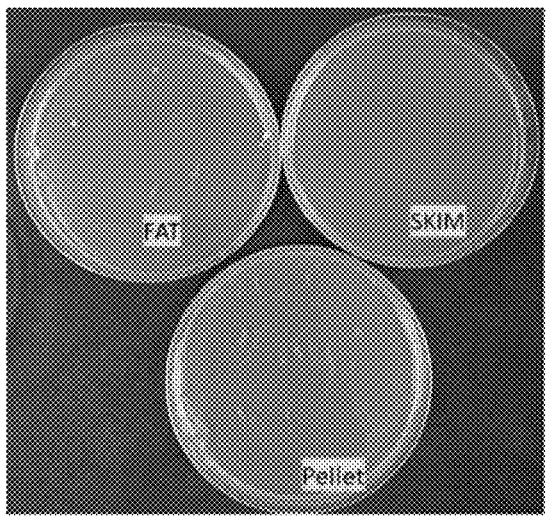
Figure 7C:
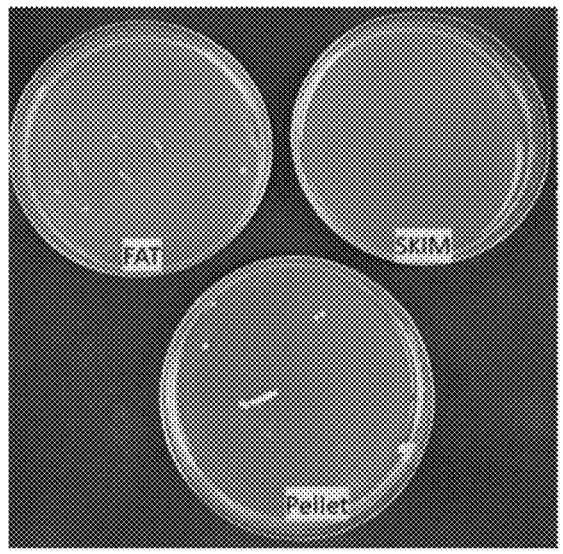

Effect of Temperature of the Sample Prior to Centrifugation on Microbial Growth of the Fat, Skim and Pellet Fractions A loopful of Golden Rule (G) and Fond du Lac (F) raw milk were streaked across TSA plates prior to any treatment or centrifugation and grown for 48 hrs at 37° C. As with FIGS. 1A-1B, microbial growth was observed for all samples where Golden Rule Farms shows substantially more growth (FIGS. 6A-6B).

1 mL of Golden Rule (G) and Fond du Lac (F) raw milk was centrifuged at a low speed setting of 2500×g for 5 minutes followed by a skim milk transfer (presumably containing the bacterial cells) to a new tube (leaving the fat layer behind) and a subsequent centrifugation at 16,000×g for 5 minutes to pellet the bacterial cells. The skim milk was removed leaving the pellet. The fat, skim and pellet fractions from Fond du Lac (F) and Golden Rule (G) raw milk incubated prior to centrifugation at 4° C., 25° C., and 37° C. were streaked on TSA plates and checked for microbial growth after 48 hrs at 37° C. (FIGS. 7A-7C, 8A-8C). The plate growth shows that there are bacteria remaining in the fat layer at all pre-centrifugation temperatures.

EXAMPLE 4

PCR Amplification Using Unpurified DNA from the Microbial Pellet

A first PCR reaction amplifies about 14 of the unpurified DNA from the pelleted raw milk sample. About 1 µL of the product of that first PCR reaction is used as the template for a second PCR reaction in which a fluorescent dye label is attached to the DNA to detect the PCR product when it binds by hybridization to the microarray. The primer sequences for the first and second PCRs are shown in Table 3. Utilizing this two-step PCR obviates the need to purify the DNA from the microbial pellet to be analyzed. The primers for the first PCR reaction are optimized to amplify the raw starting material and the primer pairs for the second PCR are optimized to obtain maximal DNA yield and to labeling from the product of the first reaction. Taken in the aggregate, the sum of the two reactions obviates the need to either purify or characterize the mastitis-causing microbial DNA of interest. Subsequently, the DNA amplified and labeled in the second PCR reaction is hybridized to probes on the microarray. Probes for the 16S locus are shown in Table 4 and probes for the ITS2 locus are shown in Table 5.

The following references are cited herein.

1. Lima et al. PLoS One, 13(3):e0193671 (Mar. 21, 2018).
2. Douellou et al. Front Microbiol., 9:947 (May 15, 2018).
3. Tobin et al. J Vis Exp., 133:56974 (Mar. 23, 2018).

What is claimed is:

1. A method for diagnosing a bovine mastitis infection in a dairy cow, comprising the steps of:
   obtaining a raw milk sample from the dairy cow;
   emulsifying a fat complement of the raw milk sample;
   centrifuging the milk sample twice to separate a microbial pellet from the raw milk sample;
   isolating total nucleic acids from the pellet comprising DNA and non-DNA nucleic acids;
   amplifying in a first PCR reaction unpurified microbial DNA in the total nucleic acids with at least one primer pair selective for at least one bovine mastitis-causing microbe-specific DNA to yield at least one bovine mastitis-causing microbe-specific amplicons; said bovine mastitis-causing microbe-specific DNA comprises bovine mastitis-causing bacterial DNA, bovine mastitis-causing fungal DNA or a combination thereof;
   amplifying in a second PCR reaction the bovine mastitis-causing microbe-specific amplicons as templates with at least one fluorescent labeled primer pair to yield fluorescent-labeled amplicons;
   hybridizing the fluorescent-labeled amplicons with mastitis-causing microbe species-specific gene probes selected from the group consisting of mastitis-causing bacterial oligonucleotide probes selected from the group consisting of SEQ ID NOS: 37-53, mastitis-causing fungal oligonucleotide probes selected from the group consisting of SEQ ID NOS: 54-61 and a combination thereof, said mastitis-causing microbe species-specific gene probes immobilized at specific known positions on the microarray;
   imaging the microarray to detect fluorescent signals from the hybridized fluorescent-labeled amplicons at the specific known positions; and
   correlating the position of the fluorescent signals on the microarray to a presence of the specific bovine mastitis-causing microbe in the raw milk, thereby diagnosing the bovine mastitis infection in the dairy cow.

2. The method of claim 1, further comprising diagnosing drug resistance in the bovine mastitis-causing microbe from hybridization of the DNA to a microbial species-specific drug resistance gene.

3. The method of claim 2, wherein the microbial species specific drug resistance gene is a beta-lactamase gene.

4. The method of claim 1, wherein a first centrifuging speed is about 400×g and a second centrifuging speed is about 8,000×g.

5. The method of claim 1, wherein the bovine mastitis-causing microbe species specific gene probes are DNA sequences or partial DNA sequences of the mastitis-causing microbes to be identified or DNA sequences complementary or homologous thereto.

6. The method of claim 1, wherein the bovine mastitis-causing microbe is a bacterium *Staphylococcus aureus, Streptococcus agalactiae, Streptococcus dysgalactiae, Streptococcus uberis, Enterococcus faecalis, Enterococcus faecium, Corynebacterium bovis, Trueperella pyogenes, Peptoniphilus indolicus, Arcanobacterium pyogenes, Escherichia coli, Klebsiella oxytoca, Klebsiella pneumoniae, Serratia marcescens, Mycoplasma bovis, Mycoplasma alkalescens, Mycoplasma bovigenitalium, Mycoplasma canadense, Mycoplasma californicum*, and *Mannheimia haemolitica*.

7. The method of claim 1, wherein the bovine mastitis-causing microbe is a fungus *Aspergillus fumigatus* or a *Candida* spp.

8. The method of claim 1, wherein a detectable concentration of the bovine mastitis-causing microbe in the raw milk sample is about $10^2$ CFU/ml.

* * * * *